US011919531B2

(12) United States Patent
Reiley et al.

(10) Patent No.: US 11,919,531 B2
(45) Date of Patent: Mar. 5, 2024

(54) METHOD FOR CUSTOMIZING MOTION CHARACTERISTICS OF AN AUTONOMOUS VEHICLE FOR A USER

(71) Applicant: DIRECT CURRENT CAPITAL LLC, Wilmington, DE (US)

(72) Inventors: Carol Reiley, Mountain View, CA (US); Fabien Blanc-Paques, Mountain View, CA (US); Gahl Levy, Mountain View, CA (US); Bradley Perry, Mountain View, CA (US); Chih Hu, Mountain View, CA (US); Vineet Jain, Mountain View, CA (US); Chip J. Alexander, Mountain View, CA (US); Alex Tomala, Mountain View, CA (US)

( * ) Notice: Subject to any disclaimer, the term of this patent is extended or adjusted under 35 U.S.C. 154(b) by 742 days.

(21) Appl. No.: 16/264,566

(22) Filed: Jan. 31, 2019

(65) Prior Publication Data
US 2019/0232974 A1    Aug. 1, 2019

Related U.S. Application Data

(60) Provisional application No. 62/624,216, filed on Jan. 31, 2018.

(51) Int. Cl.
*B60W 50/08* (2020.01)
*A61B 5/00* (2006.01)
(Continued)

(52) U.S. Cl.
CPC ....... *B60W 50/085* (2013.01); *A61B 5/02416* (2013.01); *A61B 5/165* (2013.01);
(Continued)

(58) Field of Classification Search
CPC .................................................. B60W 50/085
See application file for complete search history.

(56) References Cited

U.S. PATENT DOCUMENTS 9,507,346 B1 * 11/2016 Levinson ............. G05D 1/0291
9,539,999 B2 *  1/2017 Tseng .................... B60W 30/00
(Continued)

FOREIGN PATENT DOCUMENTS

CN    106627589 A  *  5/2017
CN    107117176 A  *  9/2017  ............ B60W 40/08
(Continued)

*Primary Examiner* — Redhwan K Mawari
(74) *Attorney, Agent, or Firm* — Polsinelli PC

(57) ABSTRACT

One variation of a method for customizing motion characteristics of an autonomous vehicle for a user includes: accessing a baseline emotional state of the user following entry of the user into the autonomous vehicle at a first time proximal a start of a trip; during a first segment of the trip, autonomously navigating toward a destination location according to a first motion planning parameter, accessing a second emotional state of the user at a second time, detecting degradation of sentiment of the user based on differences between the baseline and second emotional states; and correlating degradation of sentiment of the user with a navigational characteristic of the autonomous vehicle; modifying the first motion planning parameter of the autonomous vehicle to deviate from the navigational characteristic; and, during a second segment of the trip, autonomously navigating toward the destination location according to the revised motion planning parameter.

22 Claims, 3 Drawing Sheets

(51) Int. Cl.
*A61B 5/024* (2006.01)
*A61B 5/16* (2006.01)
*B60W 50/00* (2006.01)
*G05D 1/00* (2006.01)
*G06F 3/01* (2006.01)
*G06V 20/59* (2022.01)
*G06V 40/10* (2022.01)
*G06V 40/16* (2022.01)
*G06V 40/19* (2022.01)
*A61B 5/18* (2006.01)

(52) U.S. Cl.
CPC ....... *A61B 5/6893* (2013.01); *B60W 50/0098* (2013.01); *G05D 1/0088* (2013.01); *G05D 1/0221* (2013.01); *G05D 1/0287* (2013.01); *G06F 3/012* (2013.01); *G06F 3/013* (2013.01); *G06V 20/59* (2022.01); *G06V 40/10* (2022.01); *G06V 40/161* (2022.01); *G06V 40/168* (2022.01); *G06V 40/19* (2022.01); *A61B 5/18* (2013.01); *A61B 2503/12* (2013.01); *B60W 2050/0026* (2013.01); *B60W 2400/00* (2013.01); *B60W 2420/42* (2013.01); *B60W 2540/22* (2013.01); *G06F 2203/011* (2013.01); *G06V 40/15* (2022.01)

(56) References Cited

U.S. PATENT DOCUMENTS

| | | | | |
|---|---|---|---|---|
| 9,606,539 | B1* | 3/2017 | Kentley | G08G 1/005 |
| 10,179,588 | B2* | 1/2019 | Takamatsu | G05D 1/0234 |
| 10,748,025 | B2* | 8/2020 | Aoki | G06K 9/00234 |
| 10,807,594 | B2* | 10/2020 | Hatano | B60W 30/16 |
| 10,877,999 | B2* | 12/2020 | Bielby | G06F 16/285 |
| 10,988,142 | B1* | 4/2021 | Mehrotra | B60W 40/068 |
| 11,061,972 | B2* | 7/2021 | Ogawa | G06F 11/3438 |
| 2003/0021468 | A1* | 1/2003 | Jia | G06T 11/001 382/162 |
| 2014/0201126 | A1* | 7/2014 | Zadeh | A61B 5/165 706/52 |
| 2015/0053066 | A1* | 2/2015 | Hampiholi | B60K 37/06 84/602 |
| 2016/0378112 | A1* | 12/2016 | Ljubuncic | G06K 9/00845 701/45 |
| 2017/0123428 | A1* | 5/2017 | Levinson | G01S 7/497 |
| 2017/0150930 | A1* | 6/2017 | Shikii | A61B 5/7278 |
| 2017/0157521 | A1* | 6/2017 | Comploi | G05D 1/0088 |
| 2017/0200449 | A1* | 7/2017 | Penilla | G10L 15/063 |
| 2017/0206913 | A1* | 7/2017 | Nahman | G10L 21/007 |
| 2017/0293356 | A1* | 10/2017 | Khaderi | A61B 3/024 |
| 2017/0308082 | A1* | 10/2017 | Ullrich | G05D 1/0061 |
| 2018/0004213 | A1* | 1/2018 | Absmeier | B60W 10/18 |
| 2018/0011494 | A1* | 1/2018 | Zhu | B60W 10/18 |
| 2018/0079429 | A1* | 3/2018 | Prokhorov | H04B 1/3822 |
| 2018/0164806 | A1* | 6/2018 | Pulling | G06Q 30/0601 |
| 2018/0225551 | A1* | 8/2018 | Lin | B60H 3/0035 |
| 2018/0253109 | A1* | 9/2018 | Fontaine | G05D 1/0291 |
| 2018/0326982 | A1* | 11/2018 | Paris | G08G 1/166 |
| 2019/0008437 | A1* | 1/2019 | Ben-Ezra | A61B 5/165 |
| 2019/0088148 | A1* | 3/2019 | Jacobus | G08G 1/096716 |
| 2019/0152492 | A1* | 5/2019 | el Kaliouby | G06V 40/172 |
| 2019/0220010 | A1* | 7/2019 | Leonard | G05D 1/0088 |
| 2020/0017117 | A1* | 1/2020 | Milton | G08G 1/0112 |
| 2020/0356608 | A1* | 11/2020 | Ogawa | G06F 3/167 |
| 2021/0209388 | A1* | 7/2021 | Ciftci | G06K 9/00718 |
| 2021/0312725 | A1* | 10/2021 | Milton | G07C 5/008 |

FOREIGN PATENT DOCUMENTS

| | | | | |
|---|---|---|---|---|
| CN | 110103872 A | * | 8/2019 | B60Q 9/00 |
| GB | 2528083 A | * | 1/2016 | B60W 50/0098 |
| JP | 2016110449 A | * | 6/2016 | B60W 40/09 |
| JP | 2018538647 A | * | 12/2018 | |
| KR | 20180114103 A | * | 10/2018 | G05D 1/0293 |
| WO | WO-2016035268 A1 | * | 3/2016 | B60W 30/14 |
| WO | WO-2017079341 A2 | * | 5/2017 | G05D 1/0248 |
| WO | WO-2017189203 A1 | * | 11/2017 | A61B 5/6893 |

* cited by examiner

METHOD FOR CUSTOMIZING MOTION CHARACTERISTICS OF AN AUTONOMOUS VEHICLE FOR A USER

CROSS-REFERENCE TO RELATED APPLICATIONS

This Application claims the benefit of U.S. Provisional Application No. 62/624,216, filed on 31 Jan. 2018, which is incorporated in its entirety by this reference.

TECHNICAL FIELD

This invention relates generally to the field of autonomous vehicles and more specifically to a new and useful method for customizing motion characteristics of an autonomous vehicle for a user in the field of autonomous vehicles.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
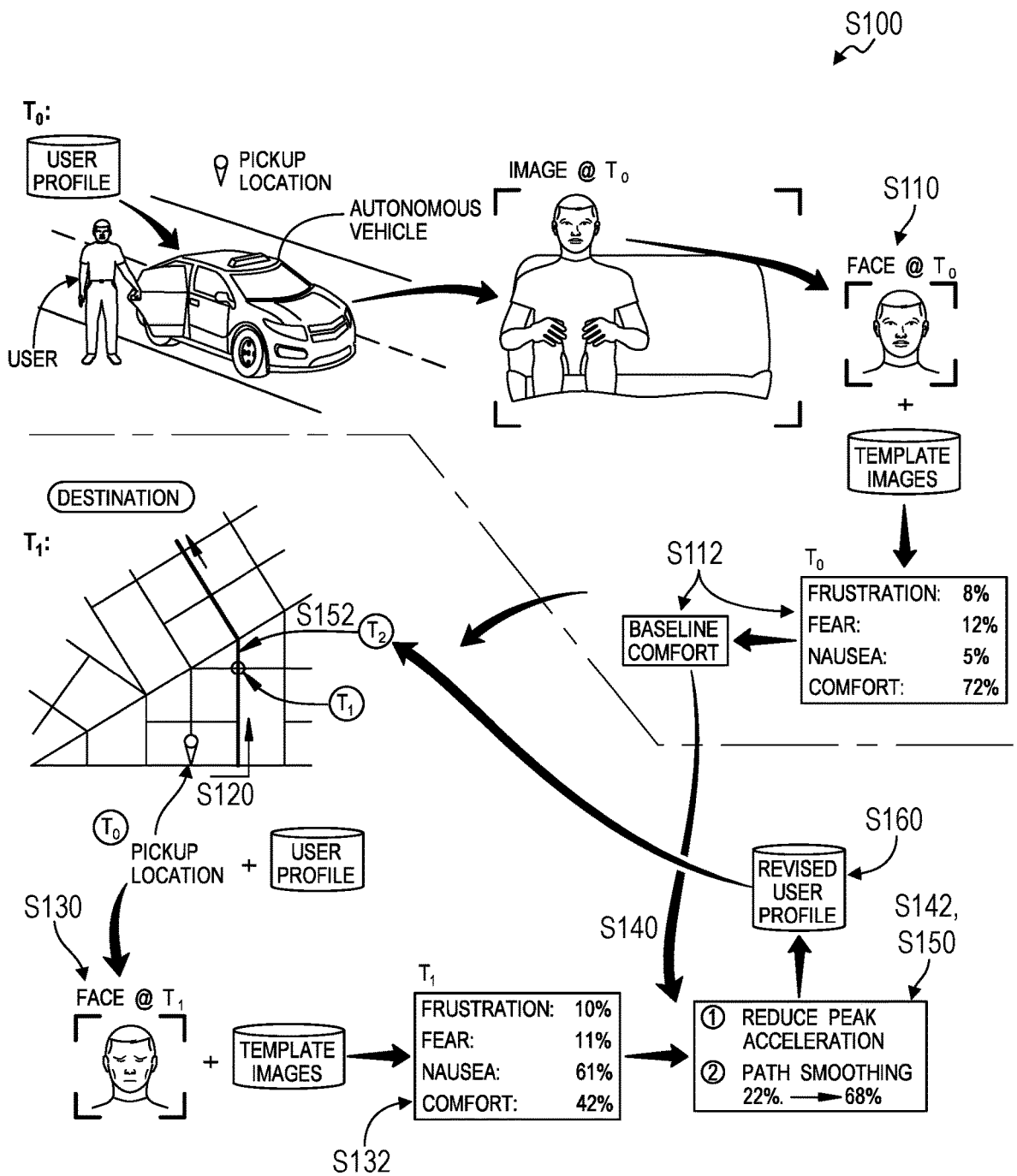
FIG. 1 is a flowchart representation of a method.

As shown in FIG. 1, a method S100 for customizing motion characteristics of an autonomous vehicle for a user includes: detecting a first set of biosignals of the user following entry of the user into the autonomous vehicle at a first time proximal a start of a trip in Block S110; and identifying a baseline emotional state of the user based on the first set of biosignals in Block S112. The method S100 also includes, during a first segment of the trip: autonomously navigating toward a destination location of the trip according to a first motion planning parameter in Block S120; detecting a second set of biosignals of the user at a second time in Block S130; identifying a second emotional state of the user based on the second set of biosignals in Block S132; detecting a degradation of sentiment of the user based on a difference between the baseline emotional state and the second emotional state in Block S140; and correlating the degradation of sentiment of the user with a navigational characteristic of the autonomous vehicle proximal the second time in Block S142. The method S100 further includes: modifying the first motion planning parameter of the autonomous vehicle to define a second motion planning parameter deviating from the navigational characteristic in Block S150; and during a second segment of the trip, autonomously navigating toward the destination location according to the second motion planning parameter in Block S122.

One variation of the method S100 includes: accessing a baseline emotional state of the user following entry of the user into the autonomous vehicle at a first time proximal a start of a trip in Block S112; and, during a first segment of the trip, generating a first sequence of navigational actions according to a first motion planning parameter, executing the first sequence of navigational actions to autonomously navigate toward a destination location in Block S120, accessing a second emotional state of the user at a second time in Block S132, detecting a degradation of sentiment of the user based on a difference between the baseline emotional state and the second emotional state in Block S140, and correlating the degradation of sentiment of the user with a navigational characteristic of the autonomous vehicle proximal the second time in Block S142. This variation of the method S100 also includes: modifying the first motion planning parameter of the autonomous vehicle to define a revised motion planning parameter deviating from the navigational characteristic in Block S150; and, during a second segment of the trip, generating a second sequence of navigational actions according to the second motion planning parameter and executing the second sequence of number value actions to autonomously navigate toward the destination location in Block S122.

2. Applications

Generally, the method S100 can be executed by an autonomous vehicle to automatically: collect biosignal data from a rider (hereinafter a "user") occupying the autonomous vehicle over the course of a trip; to transform these biosignal data into sentiment (e.g., emotional state, feeling) of the user; to detect a negative change in the sentiment of the user (e.g., increased fear, stress, anxiety, nausea, or frustration, etc.); to correlate this negative change with certain navigation characteristics of the autonomous vehicle (e.g., speed, acceleration, or trajectory); to modify a motion planning or navigational parameter implemented by the autonomous vehicle in order to reverse this negative change in the user's sentiment; and to implement this motion planning or navigational parameter during a remainder of the trip (and during future trips involving this user) or until modified according to further negative changes in the user's sentiment. In particular, the autonomous vehicle can automatically execute Blocks of the method S100 in order to automatically monitor a user inside the autonomous vehicle and rapidly respond to detected changes in the user's sentiment by automatically adjusting motion planning and/or navigational characteristics of the autonomous vehicle in order to maintain a high degree of user comfort throughout the trip.

Figure 2:
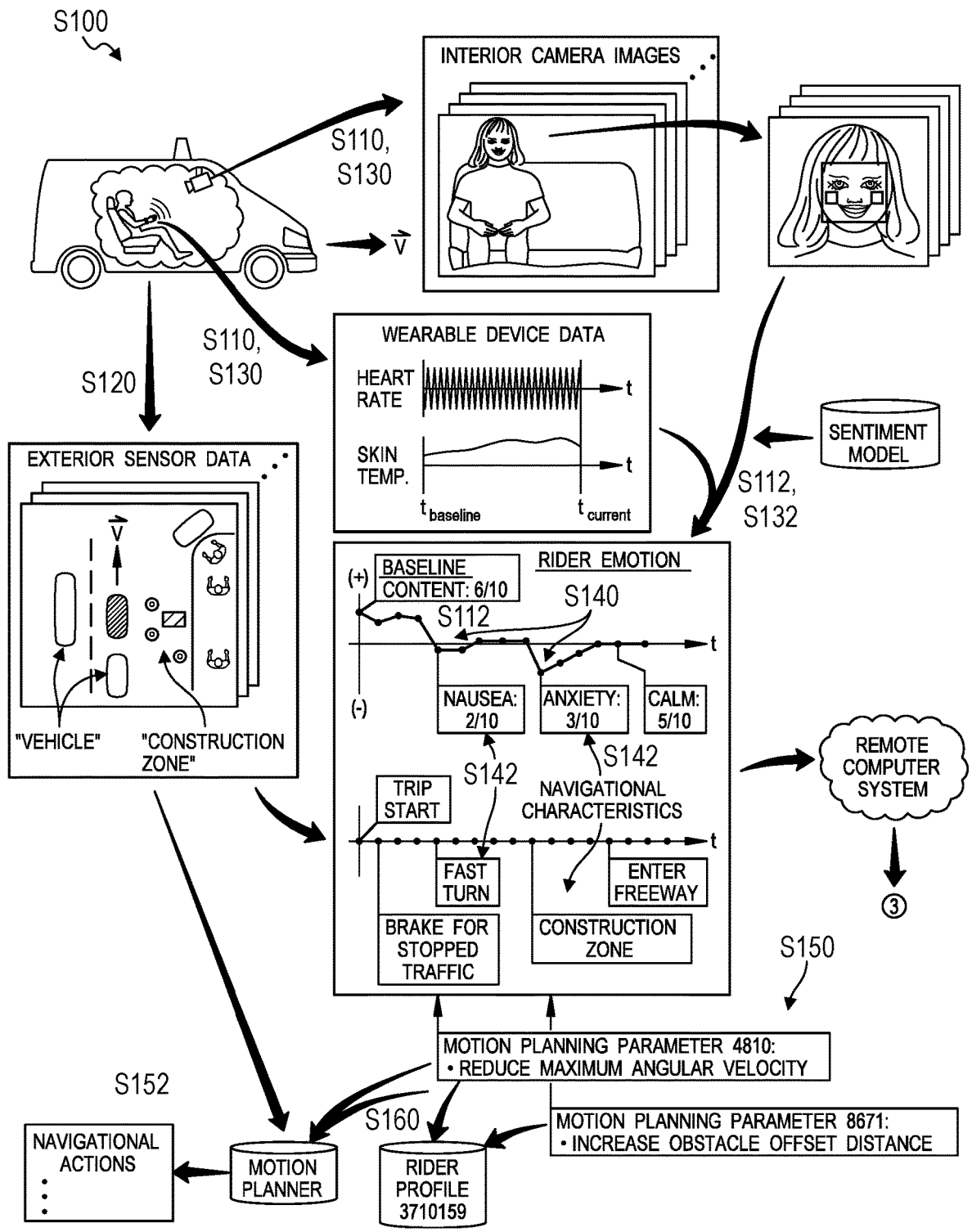
FIG. 2 is a flowchart representation of one variation of the method.

For example, the autonomous vehicle can: include an optical sensor; record images of the user during a trip through the optical sensor; and extract sentiments of the user from these images, as shown in FIG. 2. The autonomous vehicle can additionally or alternatively interface with a wearable device worn by the user to access biosignal data of the user and to transform these biosignal data into sentiments of the user. In this example, the user may exhibit increased levels of fear, stress, or anxiety as a result of perceived excess speed, perceived narrow avoidance of obstacles, or perceived aggressive navigation by the autonomous vehicle during a trip. If the autonomous vehicle detects increased levels of fear, stress, or anxiety—such as greater than a preset threshold change since the user entered the autonomous vehicle—over a short time interval (e.g., less than ten seconds), the autonomous vehicle can: associate this sentiment change with a singular action by the autonomous vehicle; scan stored navigational events at the autonomous vehicle's path over this time interval for a navigational event likely to have triggered this sentiment change (e.g., proximity of the autonomous vehicle to a pedestrian, other vehicle, construction zone, or other obstacle or contact with a curb or pothole); correlate the change in sentiment with this navigational event; and modify motion planning or navigation parameters of the autonomous vehicle in order to reduce frequency or intensity of similar events along the remainder of the trip (e.g., by increasing a minimum obstacle avoidance distance or "offset distance" for avoiding pedestrians and other vehicles, increasing a curb buffer distance, or decreasing the acceleration profile of the vehicle).

In this example, if the autonomous vehicle detects an increased level of nausea—such as greater than a preset threshold since the user entered the autonomous vehicle—in the user during the trip, the autonomous vehicle can automatically: set reduced peak permitted forward and lateral accelerations (and jerks) of the autonomous vehicle during the remainder of the trip; increase weight of a smoothing function for a motion planning model implemented by the autonomous vehicle in order to smooth a path traversed by the autonomous vehicle during the remainder of the trip; and navigate to the user's specified duration according to these revised navigation and motion planning parameters in order to reduce or abate further increase in nausea experienced by the user. Similarly, if the autonomous vehicle detects such an increased level of user nausea during the trip, the autonomous vehicle can automatically increase penalties for: control inputs (e.g., steering wheel angle change, accelerator position change, and brake position change); jerk (i.e., the derivative of acceleration); and/or rates of change of these control inputs. The autonomous vehicle can then apply these penalties to a motion planning algorithm implemented by the autonomous vehicle until these penalties are modified again responsive to data collected from the user later in the trip.

In this example, the user may alternatively exhibit frustration due to driving characteristics of the autonomous vehicle, such as perceived slow speeds, perceived slow accelerations, or perceived timidity of the autonomous vehicle. If the autonomous vehicle detects such increased level of frustration—such as greater than a preset threshold change since the user entered the autonomous vehicle—the autonomous vehicle can associate this increased frustration with a perception of timidity and adjust motion planning and navigation parameters of the autonomous vehicle accordingly, such as by: setting increased peak permitted forward and lateral accelerations (and jerks) of the autonomous vehicle during the remainder of the trip; decreasing weight of a smoothing function for a motion planning model implemented by the autonomous vehicle; and/or decreasing obstacle avoidance distances for curbs, other vehicles, and other obstacles. The autonomous vehicle can then navigate to the user's specified duration according to these revised navigation and motion planning parameters in order to reduce the user's frustration.

The autonomous vehicle can therefore actively monitor sentiment of a user occupying the autonomous vehicle while navigating to a destination and adjust motion planning and/or navigation parameters implemented by the autonomous vehicle in real-time responsive to changes in the user's sentiment in order to maintain or improve the user's comfort throughout the trip.

The autonomous vehicle can also upload motion planning and/or navigation parameters customized for the user to a user profile associated with the user, as shown in FIGS. 1 and 2. The user profile can then be accessed and implemented by the same or other autonomous vehicles during later trips involving the user, thereby automatically customizing motion planning and navigational characteristics of the autonomous vehicles for the user immediately upon entry of the user into the autonomous vehicles. These autonomous vehicles can also execute Blocks of the method S100 during these subsequent trips to further revise or update motion planning and/or navigation parameters for the user.

The autonomous vehicle can also detect multiple passengers occupying the passenger compartment during a ride and implement similar methods and techniques to generate customized planning and/or navigation parameters based on biosignals read from these multiple passengers. In one example, the autonomous vehicle calculates a discrete set of revised motion planning and/or navigation parameters for each occupant and then implements the revised planning and/or navigation parameters for the occupant exhibiting greatest sensitivity (e.g., greatest nausea, then greatest fear, then greatest frustration). Alternatively, the autonomous vehicle can combine (e.g., average) these discrete sets of revised planning and/or navigation parameters and implement these composite planning and/or navigation parameters, as described below. Yet alternatively, the autonomous vehicle can verify that a particular navigational characteristic (e.g., proximity of the autonomous vehicle to a construction zone) was a primary cause of rider sentiment degradation (e.g., increased rider anxiety) if the autonomous vehicle detects similar, concurrent rider sentiment degradation among most or all riders in the autonomous vehicle; the autonomous vehicle can then modify a corresponding motion planning parameter accordingly and implement this modified motion planning parameter during the remainder of the trip or until modified again responsive to other emotion or sentiment changes in these riders.

The autonomous vehicle can additionally or alternatively: collect feedback from the user during the trip, such as through the user's mobile computing device (e.g., smartphone) or through a display inside in the autonomous vehicle; correlate negative (and positive) feedback provided by the user to navigational events occurring at the autonomous vehicle; and automatically modify motion planning and/or navigation parameters of the autonomous vehicle accordingly substantially in real-time. The autonomous vehicle (or a remote computer system) can similarly: collect feedback from the user following completion of the trip; correlate negative (and positive) feedback provided by the user to navigational events occurring at the autonomous vehicle during the trip; and automatically update the user's profile to reflect motion planning and/or navigation parameters that may reduce negative sentiments (and reinforce position sentiments) accordingly.

The autonomous vehicle can implement similar methods and techniques: to detect positive indicators of user comfort, such as slow and consistent heart rate, relaxed facial features, facial features correlated with joy or trust, user attention to other occupants in the autonomous vehicle (i.e., rather the to motion of the autonomous vehicle), and/or transitions from negative comfort indicators to such positive comfort indicators; to reinforce current weights (or penalties) for control inputs, jerk (i.e., the derivative of acceleration), and/or rates of change of control inputs; and to then apply these reinforced weights to a motion planning algorithm to maintain the user's current high level of comfort.

Therefore autonomous vehicles and/or a remote computer system can implement Blocks of the method S100: to collect sentiment-related data from the user; to modify motion planning and/or navigation parameters according to these user sentiment data; and to implement these revised motion planning and/or navigation parameters in order to improve user comfort for occupants during trips in these autonomous vehicles.

3. Autonomous Vehicle and Trip Initialization

The autonomous vehicle can include an autonomous passenger road vehicle configured to carry one or more passengers between pickup and destination locations. For example, a user may enter a request—through a native rideshare application executing on her smartphone—for pickup at a pickup location and navigation to a destination location. Upon receipt of this request, a remote computer system can assign this trip to the autonomous vehicle, dispatch the autonomous vehicle to the pickup location, and load the user's profile (or a default profile for the user's first trip) onto the autonomous vehicle. Upon arrival at the pickup location, the autonomous vehicle can: confirm entry of the user into the autonomous vehicle; record a baseline sentiment of the user, as described below; load or calculate a route to the destination location; and resume navigation along the route according to the motion planning and/or navigation parameters stored in the user's profile. The autonomous vehicle can then execute subsequent Blocks of the method S100 to modify these motion planning and/or navigation parameters according to a change in the user's sentiment away from the baseline sentiment.

4. Real-Time Biosignal Collection and Emotion Detection

In one variation, the autonomous vehicle collects biosignal data from the user—through various sensors integrated into or connected to the autonomous vehicle—in real-time during the trip.

4.1 Wearable Device

In one implementation shown in FIG. 2, the system includes a wireless radio and interfaces with a wearable device—including biometric sensors—worn by the user to collect user biometric data via the wireless radio. For example, when creating an account for requesting rides with autonomous vehicles through the native application described above, the native application can: query the user to confirm whether she wears a wearable device; prompt the user to authorize the native application and the remote computer system to access biometric data from this wearable device; and/or prompt the user to authorize autonomous vehicles to access these data during the user's trips. Following authorization for the autonomous vehicle to access data from the user's wearable device, the remote computer system can store this authorization and an identifier of the user's wearable device in the user's profile. The autonomous vehicle can then pull or otherwise query the wearable device for biometric data from the user during the user's trip.

For example, at the beginning of the trip, the autonomous vehicle can automatically connect to the user's wearable device (e.g., via short-range wireless communication protocols); and the wearable device can regularly upload skin temperature, galvanic skin response, and/or heart rate, etc. to the autonomous vehicle (e.g., substantially in real-time) once the autonomous vehicle confirms that the user has entered the autonomous vehicle and until the autonomous vehicle arrives at the user-specified destination. Alternatively, the autonomous vehicle can automatically connect to the user's smartphone during the trip; the user's wearable device can regularly upload data to her smartphone; and the autonomous vehicle can access biosignal data from the user's wearable device via the smartphone.

Similarly, in response to entry of the user at the start of the trip, the autonomous vehicle can connect to a wearable device—including a biometric sensor and worn by the user—via short-range wireless communication protocol. The autonomous vehicle can then access (or "download") a first set of biosignals recorded and wirelessly broadcast by the wearable device proximal the start of the trip in Block S110; interpret a first user emotion from these first biosignals; later access a second set of biosignals recorded and wirelessly broadcast by the wearable device at a second time during the trip in Block S130; and then interpret a second user emotion from these second biosignals in Block S132, as described below.

Therefore, throughout the trip, the autonomous vehicle can regularly pass these biosignal data—received from the user's wearable device—into an emotion characterization model (e.g., a regression model or a neural network, etc.) that transforms these biosignal data into a sentiment (e.g., emotional state, feeling, and/or degree thereof) of the user. The autonomous vehicle can then store these derived user sentiments throughout the trip, such as by annotating the autonomous vehicle's georeferenced route throughout this trip with these sentiment values. Alternatively, the user's wearable device or smartphone can locally interpret user sentiment from these biosignal data and regularly serve these user sentiment values to the autonomous vehicle, such as once per five-second interval. However, the autonomous vehicle can interface with the user's wearable device in any other way to access or derive user sentiment values during the trip.

In this implementation, the autonomous vehicle can also store a sentiment of the user at the beginning of the trip—such as recorded just after the user entered the autonomous vehicle—as a baseline sentiment of the user. By then comparing the later wearable device-derived sentiments of the user to this baseline sentiment, the autonomous vehicle can: determine whether the autonomous vehicle's navigation has lead to the user's feelings of nausea, frustration, anxiety, or other discomfort (e.g., if the user's sentiment diminishes from the baselines sentiment over the course of the trip) or if these feelings of discomfort were present prior to the user's entry into the autonomous vehicle; and modify its motion planning and/or navigation parameters accordingly.

4.2 Integrated Camera

In another implementation shown in FIG. 2, the autonomous vehicle includes an interior-facing camera configured to record images (e.g., frames in a color video stream) of the interior of the autonomous vehicle—occupied by the user—during the trip; and the autonomous vehicle extracts user sentiment from these images. In this implementation, the autonomous vehicle can include a color (e.g., RGB) camera with a wide-angle lens and/or a depth sensor (e.g., a LIDAR or structured light sensor) defining fields of view directed toward the autonomous vehicle's interior, such as toward passenger seat areas. For example, the autonomous vehicle can include one or more such optical sensors: coupled to an interior ceiling and directed downward; or coupled to the dashboard of the autonomous vehicle and directed rearward toward the autonomous vehicle's passenger compartment. In another example, the autonomous vehicle can include an optical sensor integrated into a housing of an overhead interior map light within the autonomous vehicle's interior. However, the autonomous vehicle can include one or more optical sensors of any other type and arranged in any other way inside the autonomous vehicle.

In one implementation in which the autonomous vehicle includes multiple optical sensors, these optical sensors can be arranged inside the autonomous vehicle such that their fields of view cooperatively cover a large proportion of the passenger seat areas within the passenger compartment. In a scan cycle during the trip, the autonomous vehicle can trigger each optical sensor to record a discrete image and then stitch these discrete images into a composite 2D or 3D image based of the interior of the autonomous vehicle on known relative positions of these optical sensors. The autonomous vehicle (or the remote computer system) can then process this composite image, as described below, to detect the user and to qualify or quantify the user's sentiment during this scan cycle. Once an image of the interior of the autonomous vehicle is thus recorded, the autonomous vehicle can implement face detection, eye detection, or other computer system techniques to detect the user inside the passenger compartment. (The autonomous vehicle can also implement object tracking to track the user over multiple contiguous images output by the optical sensor(s)).

4.2.1 Photoplethysmography and Heart Rate

In one example implementation, the autonomous vehicle implements photoplethysmography or Eulerian video magnification to extract the user's heart rate from a sequence of images of the interior of the autonomous vehicle. For example, once the autonomous vehicle detects the user's face in a video feed output by the optical sensor, the autonomous vehicle can: detect cyclical variations in color intensity of pixels corresponding to the user's face (e.g., "pulsatile photoplethysmographic signals") in the video feed; and transform a frequency of these cyclical variations into the user's heart rate. The autonomous vehicle can repeat this process for a series of images recorded by the optical sensor over time in order to develop a time series of the user's heart rate throughout the trip.

Similarly, the autonomous vehicle can: record a first sequence of video frames via a camera arranged in the autonomous vehicle and facing a passenger compartment in the autonomous vehicle when the user enters the autonomous vehicle at the start of the trip; detect a face of the user in the first sequence of video frames; detect a first sequence of cyclical variations in color intensity of pixels depicting the face of the user in the first sequence of video frames; transform the first sequence of cyclical variations in color intensity into a first heart rate of the user proximal the first time in Block S110; and identify a baseline emotion state—including a baseline anxiety level of the user—at the first time based on the first heart rate in Block S112. At a subsequent time during the trip, the autonomous vehicle can then: record a second sequence of video frames via the camera; detect the face of the user in the second sequence of video frames; detect a second sequence of cyclical variations in color intensity of pixels depicting the face of the user in the first sequence of video frames; transform the second sequence of cyclical variations in color intensity into a second heart rate of the user proximal the second time in Block S130; and identify a second emotion state—representing a second anxiety level of the user—at the second time based on the second heart rate. The autonomous vehicle can then: detect increased anxiety of the user based on the difference between the baseline emotional state and the second emotional state in Block S140; and modify a motion planning parameter implemented by the autonomous vehicle in order to reduce frequency or magnitude of navigational characteristics occurring concurrently with this user sentiment degradation.

The autonomous vehicle can also correlate increases in heart rate of the user with increased stress or fear. For example, the autonomous vehicle can associate an increase in heart rate of over ten beats per minute over a period of five seconds as fear or other negative emotional response to a discrete event occurring—approximately concurrently—near the autonomous vehicle. In this example, the autonomous vehicle can associate a similar increase in the user heart rate over a longer period of time (e.g., one minute) with frustration. However, the autonomous vehicle can interpret absolute changes and/or rates of change in heart rate of the user with any other user sentiment in any other way. The autonomous vehicle can then store these heart rate and/or user sentiment values, such as by tagging segments of the current route with these heart rate and/or user sentiment values based on times that these heart rate values were recorded and geospatial locations of the autonomous vehicle at these times.

4.2.2 Eye Tracking and Nausea

In another example implementation, the autonomous vehicle can detect the user's eyes in images output by the optical sensor, detect rapid eye movements in these images, and interpret these rapid eye movements as degrees of user nausea throughout the trip. For example, the autonomous vehicle can: implement eye tracking techniques to detect the user's eyes in a video feed output by the optical sensor; extract a rate (and amplitude) of oscillations of the users eyes from these images; correlate this rate (and amplitude) of eye oscillations with a degree to which the user may be nauseated; and repeat this process throughout the trip in order to develop a georeferenced time series of the degree of the user's nausea.

Similarly, the autonomous vehicle can: record a first sequence of video frames via a camera arranged in the autonomous vehicle and facing a passenger compartment in the autonomous vehicle when the user enters the autonomous vehicle at the start of the trip; detect eyes of the user in the first sequence of video frames; detect a first sequence of rapid eye movements of the user in the first sequence of video frames in Block S110; estimate a first degree of nausea of the user at the start of the trip based on a first rate of eye movements in the first sequence of rapid eye movements; and store the first degree of nausea of the user as the baseline emotion state of the user in Block S112. Subsequently, the autonomous vehicle can: record a second sequence of video frames via the camera; detect eyes of the user in the second sequence of video frames; detect a second sequence of rapid eye movements of the user in the second sequence of video frames in Block S130; estimate a second degree of nausea of the user at this later time based on a second rate of eye movements in the second sequence of rapid eye movements; and store the second degree of nausea of the user as the second emotion state of the user in Block S132. Thus, the autonomous vehicle can detect increased nausea of the user based on a difference between the baseline emotional state and the second emotional state in Block S140.

4.2.3 Template Matching

In yet another example implementation shown in FIG. 1, the autonomous vehicle extracts user sentiment directly from images output by the optical sensor. For example, the autonomous vehicle can: implement computer vision techniques—such as face detection and template matching—to detect the user's face in an image recorded by the optical sensor; and implement template matching techniques to match features of the user's face to a template image representing a known sentiment (e.g., calm, anxious, nauseated, fearful, etc.). Alternatively, the autonomous vehicle can: extract features from a region of the image coinciding with the user's face; and pass these features through an emotion characterization model to predict the user's sentiment at the time this image was recorded.

The autonomous vehicle can repeat this process for a series of images recorded by the optical sensor throughout the trip in order to develop a georeferenced time series of user sentiments (and degrees of these sentiments).

4.2.4 Sentiment Model

Similarly, the autonomous vehicle can: record a first sequence of video frames via a camera arranged in the autonomous vehicle and facing a passenger compartment in the autonomous vehicle; detect a face of the user in the first sequence of video frames; extract a first facial characteristic of the user from the first sequence of video frames in Block S110; and pass the first facial characteristic into an emotion characterization model (or "sentiment model") to identify the baseline emotional state of the user proximal the first time in Block S112, as shown in FIG. 2. The autonomous vehicle can later: record a second sequence of video frames via the camera during a next segment of the trip; detect the face of the user in the second sequence of video frames; extract a second facial characteristic of the user from the second sequence of video frames in Block S130; and pass the second facial characteristic into the emotion characterization model to identify the second emotional state of the user during this time in Block S132.

As described below, the autonomous vehicle can then: detect transition from the baseline emotional state including a positive emotion (e.g., excited, elated, ecstatic, calm, serene, or content) to the second emotional state including a negative emotion (e.g., angry, anxious, scared, sad, bored, tired); and modify a motion planning parameter implemented by the autonomous vehicle to reduce frequency of magnitudes of navigational events occurring concurrently with this degradation in user sentiment. Alternatively, if the autonomous vehicle detects that the user has transitioned from the baseline emotional state including a high-intensity positive emotion (e.g., excited, elated, or ecstatic) to the second emotional state including a low-intensity positive emotion (e.g., calm, serene, or content), the autonomous vehicle can: predict that the user is comfortable and calm in the autonomous vehicle; and maintain current motion planning parameters accordingly.

5. Sentiment Change Response

The autonomous vehicle can: store a baseline sentiment of the user; regularly compare the user's current sentiment to the stored baseline sentiment (or the last sentiment of the user) for the current trip; and selectively adjust motion planning parameters implemented by the autonomous vehicle in (near) real-time responsive to these sentiment deviations.

5.1 Baseline Sentiment

As described above, the autonomous vehicle can also store a sentiment of the user—derived from an image of the passenger compartment recorded just after the user entered the autonomous vehicle—as a baseline sentiment of the user, as shown in FIGS. 1 and 2. The autonomous vehicle can then respond to negative deviations in the user's sentiment from this baseline sentiment by modifying its motion planning and/or navigation parameters, as described below.

5.2 Absolute Sentiment Change Response

The autonomous vehicle can regularly compare the user's current sentiment to the stored baseline sentiment for the current trip and respond to these deviations in real-time. In one implementation, if the autonomous vehicle detects an increase in frustration in the user above a baseline frustration, the autonomous vehicle can increase peak permitted accelerations in forward, reverse, and lateral directions. In another implementation, if the autonomous vehicle determines that the user's level of nausea has increased, the autonomous vehicle can reduce peak permitted accelerations in forward and lateral directions and increase weight of a smoothing function for a path planning model implemented by the autonomous vehicle in order to smooth a path traversed by the autonomous vehicle during the remainder of the trip.

In another implementation shown in FIG. 2, if the autonomous vehicle determines that the user's fear, stress, or anxiety has increased, the autonomous vehicle can increase an obstacle avoidance distance and reduce peak permitted speed (or reduce peak permitted speed relative to posted speed limits) of the autonomous vehicle. For example, the autonomous vehicle can: autonomously navigate past a fixed obstacle at a first offset distance according to a current motion planning parameter at a particular time during the trip; detect degradation of user sentiment in the form of increased fear, increased stress, or increased anxiety over a short time interval leading up to or spanning the particular time in Block S140; and correlate navigation by the autonomous vehicle past the fixed obstacle at the first offset distance (the "navigational characteristic" of the autonomous vehicle) with degradation of sentiment of the user (e.g., increased fear, increased stress, or increased anxiety in the user) in Block S142. The autonomous vehicle can then modify the motion planning parameter (or generate a new motion planning parameter) that specifies a second offset distance greater than the first offset distance.

In a similar example, the autonomous vehicle can: brake at a first rate and over a first distance according to a current motion planning parameter while approaching stopped (or slow) traffic ahead over a short time interval during the trip; detect degradation of user sentiment in the form of increased fear, increased stress, or increased anxiety over this time interval in Block S140; and correlate deceleration at the first rate and/or over the first distance when approaching stopped traffic ahead (the "navigational characteristic" of the autonomous vehicle) with degradation of sentiment of the user (e.g., increased fear, increased stress, or increased anxiety in the user) in Block S142. The autonomous vehicle can then modify the motion planning parameter (or generate a new motion planning parameter) that specifies deceleration at a second rate less than the first rate and/or deceleration over a second distance greater than the first distance when approaching stopped traffic ahead.

Similarly, the autonomous vehicle can: autonomously navigate through a turn at a first steering angle and at a first speed—thereby yielding a first angular velocity according to a current motion planning parameter—over a short time interval during the trip; detect degradation of user sentiment in the form of increased fear, increased stress, increased anxiety, or increased nausea over this time interval in Block S140; and correlate the first angular velocity (the "navigational characteristic" of the autonomous vehicle) with degradation of sentiment of the user (e.g., increased fear, increased stress, increased anxiety, or increased nausea in the user) in Block S142. The autonomous vehicle can then modify the motion planning parameter (or generate a new motion planning parameter) that specifies a second maximum permitted angular velocity less than the first angular velocity when executing turns.

In another implementation, if the autonomous vehicle determines that the user's level of nausea has increased, the autonomous vehicle can reduce peak permitted accelerations in forward and lateral directions and increase weight of a smoothing function for a motion planning model implemented by the autonomous vehicle in order to smooth a path traversed by the autonomous vehicle during the remainder of the trip.

In yet another implementation, if the autonomous vehicle detects an increase in frustration of the user above a baseline frustration, the autonomous vehicle can increase peak permitted accelerations in forward, reverse, and lateral directions.

The autonomous vehicle can then implement these adjusted motion planning and/or navigation parameters immediately until the conclusion of the trip. The autonomous vehicle can also write these adjusted motion planning and/or navigation parameters to the user's profile, such as in real-time or upon conclusion of the trip.

The autonomous vehicle can repeat this process regularly throughout the trip. Also, if the autonomous vehicle determines that the user's sentiment has improved since the user entered the autonomous vehicle, the autonomous vehicle can reset the baseline sentiment for this trip to this improved sentiment and implement this revised baseline sentiment for the remainder of the trip or until revised again.

Furthermore, the autonomous vehicle can upload the trip and user sentiment data—such as in the form of a sentiment-annotated georeferenced route—to the remote computer system for further processing, extraction of correlations between sentiment and navigational characteristics, and further revision of motion planning and/or navigation parameters written to the user's profile.

5.3 Rate of Sentiment Change

In another implementation the autonomous vehicle can: derive rates of sentiment change of the user; link rapid user sentiment changes with navigation characteristics of the autonomous vehicle occurring over short periods of time (e.g., by correlating rapid increases in user anxiety with rapid braking, the autonomous vehicle passing a construction zone with minimal distance offset, or merging into traffic); link slow user sentiment changes with longer-term navigation characteristics of the autonomous vehicle (e.g., by correlating a slow increase in user anxiety with excessive acceleration, angular velocities, and jerk); and then selectively adjust motion planning parameters during the remainder of the trip to improve user sentiment or prevent further user sentiment degradation (e.g., by braking soon, increasing offset distances from construction zones, merging into traffic slower, or increasing weight of a smoothing function for executing navigational actions).

For example, during the trip, the autonomous vehicle can: implement a path planning model to generate a sequence of navigational actions; apply a smoothing function at a first weight—defined by a motion planning parameter—to transition between navigational actions in the sequence of navigational actions; and execute this sequence of navigational actions—smoothed according to the motion planning parameter—to autonomously navigate toward a destination location of the trip. Throughout this trip, the autonomous vehicle can also: record a timeseries of navigational events at the autonomous vehicle during the trip; record a timeseries of user emotions or sentiments during the trip; and calculate a rate of change (e.g., degradation) of sentiment of the user during the trip (e.g., based on the timeseries of user emotions). Then, in this example, if the rate of change of degradation of the current sentiment of the user remains below a threshold rate of change (and if an absolute change of the user's sentiment from the baseline sentiment exceeds a threshold magnitude), the autonomous vehicle can: correlate the current degradation of sentiment of the user with a first jerk maximum (the "navigational characteristic") exhibited by the autonomous vehicle during the trip in Block S142; modify the motion planning parameter to increase the weight of the smoothing function in Block S150; and then implement this modified motion planning parameter to reduce the peak jerk experienced by the user during the remainder of the trip. In particular, if the autonomous vehicle demines that the user's nausea has slowly increased over the duration of the trip, the autonomous vehicle can modify the path planning parameter to smooth navigational actions executed by the autonomous vehicle, which may alleviate the user's nausea.

However, in this example, if the rate of change of degradation of the current sentiment of the user exceeds the threshold rate of change (and if the absolute change of the user's sentiment from the baseline sentiment exceeds a threshold magnitude), the autonomous vehicle can: predict an association between the degradation of sentiment and a singular navigational event by the autonomous vehicle; scan the timeseries of navigational events for a particular navigational event occurring proximal a time that this rate of sentiment degradation exceeded the threshold rate of change; and correlate this degradation of sentiment of the user with a navigational characteristic that produced or is otherwise associated with the particular navigational event. Accordingly, the autonomous vehicle can define or refine a motion planning parameter that is predicted to reduce the frequency of similar navigational events (i.e., navigational events analogous to the particular navigational event). Therefore, if the autonomous vehicle detects a rapid increase in the user's fear or anxiety (which may manifest as similar facial expression, heart rate, heart rate variability, and/or skin temperature changes as increased nausea), the autonomous vehicle can predict that an individual navigational event produced this degradation of user sentiment and modify the motion planning parameter to avoid similar or analogous situations in the future.

6. Grab Handles

In yet another example implementation, the autonomous vehicle includes a passenger grab handle arranged inside the passenger compartment. The autonomous vehicle can also include: a position sensor coupled to the grab handle and configured to detect selection of the grab handle; and/or a force sensor configured to detect a magnitude of force applied to the grab handle. The autonomous vehicle can thus predict user anxiety or fear based on outputs of the position and/or force sensors. For example, the autonomous vehicle can regularly sample these sensors during the user's trip. In this example, because the user may brace herself against the grab handle in preparation for a perceived impact, the autonomous vehicle can predict increased user anxiety or fear if: the autonomous vehicle is in motion; a duration of use of the grab handle exceeds a threshold duration; and/or a force applied to the grab handle exceeds a threshold magnitude.

The autonomous vehicle can then scan a scene nearby for an approaching or nearby vehicle, pedestrian, or other obstacle that may be result of the user's increased fear and increase an obstacle avoidance distance for the user if such an obstacle is detected; if not, the autonomous vehicle can associate the user's increased fear with a speed of the autonomous vehicle and automatically reduce its current speed accordingly.

The autonomous vehicle can therefore regularly sample the position and/or force sensors in the grab handle, correlate outputs of these sensors with increased user anxiety or fear, and store times and durations of these grab handle events—and predicted instances of elevated user fear—such as by annotating the autonomous vehicle's georeferenced route toward the user specified destination.

In this implementation, the grab handle can also include a heart rate monitor, skin temperature sensor, or biometric sensor; and the autonomous vehicle computer network reach biosignals from the user through the grab handle when gripped by the user and implement methods and techniques described above to modify motion planning and/or navigation parameters accordingly.

In a similar example, the autonomous vehicle can: detect selection of a grab handle in the passenger compartment by the user while the autonomous vehicle is in motion; interpret selection of the grab handle by the user as an increase in anxiety of the user; scan a scene near the autonomous vehicle for an object approaching the autonomous vehicle (e.g., based on data collected by exterior-facing sensors on the autonomous vehicle) at the current time; predict an association between the increase in anxiety of the user and the object; modify a motion planning parameter of the autonomous vehicle to increase a target offset distance from external objects in response to this association between user anxiety and the approaching object; and then navigate past the object at this new target offset distance according to the updated motion planning parameter.

The autonomous vehicle can implement similar methods and techniques to collect and respond to user biosignal data via other sense-enabled surfaces within the passenger compartment, such as an armrest, a center console surfaces, a seat surface, etc.

However, the autonomous vehicle can automatically collect user-related data during the trip and can implement any other method or techniques to interpret or estimate the user's sentiment at corresponding times based on these user-related data.

7. Direct Feedback

In one variation, the autonomous vehicle collects sentiment feedback from the user directly through surveys.

7.1 Selective Surveys

In one implementation, the autonomous vehicle presents sentiment-related surveys to the user throughout the trip, such as through the native application executing on the user's mobile computing device, as described above, or through a user interface (e.g., a touch display) arranged inside the passenger compartment.

In one implementation, the autonomous vehicle serves sentiment-related surveys to the user intermittently, such as in response to the autonomous vehicle approaching and/or passing select types of obstacles, intersections, or other navigational actions during the trip. For example, as the autonomous vehicle approaches a known construction zone or other obstacle in or near the roadway (e.g., approximately one half mile or 500 meters ahead of the autonomous vehicle), the autonomous vehicle can prompt the user to indicate her current comfort level at a first time. The autonomous vehicle can again survey the user for her sentiment at a second time once the autonomous vehicle passes the obstacle, such as within 50 meters of the autonomous vehicle passing the construction zone. In this example, if the user's comfort diminished significantly from the first time to the second time, the autonomous vehicle can predict that the autonomous vehicle navigated too close to the obstacle for the user's comfort and then increase an obstacle avoidance distance implemented by the autonomous vehicle during the remainder of the current trip accordingly. (The autonomous vehicle can also store this increased obstacle avoidance distance in the user's profile, which other autonomous vehicles can implement to tailor their navigation characteristics to the user when the user is occupying these other autonomous vehicles in the future.) However, if the user's responses to these surveys indicate that the user's comfort level had not changed over this period of time or if the user neglected to respond to the second survey—which may also indicate that the user's comfort level has not changed—the autonomous vehicle can preserve the current obstacle avoidance distance or even reduce the obstacle avoidance distance in order to simplify future motion planning by the autonomous vehicle during the current trip.

In this example, the autonomous vehicle can store the user's responses in memory, such as by tagging segments of the current route with survey responses based on times that these responses were submitted by the user and geospatial locations of the autonomous vehicle at these times.

Therefore, the autonomous vehicle can survey the user for her comfort level as the autonomous vehicle approaches a known or detected obstacle or key road feature, such as: a construction zone; a busy or difficult intersection; an unprotected left turn; a right turn on red; a school zone; a highway on-ramp or off-ramp; a large pothole; etc. The autonomous vehicle can then derive a change in navigation parameters of the autonomous vehicle to improve the user's comfort based on the user's responses to these surveys. The autonomous vehicle can also survey the user upon initial entry into the autonomous vehicle and store a sentiment extracted from the user's feedback to this initial survey as a baseline sentiment.

7.2 Continuous and Regular Surveys

In another implementation, the autonomous vehicle can regularly or continuously serve a query to the user for sentiment-related feedback For example, the autonomous vehicle can render a query including "how was my driving over the last minute?" and qualitative or qualitative measures (e.g., a quantitative scale of "1" through "5" of a qualitative scale of "great" to "terrible") on a display facing the user's seat inside the autonomous vehicle. In a similar example, the autonomous vehicle can render a query including "how are you feeling?" and possible qualitative responses (e.g., "nauseated," "fearful," "bored," "fine," "great"). If the user fails to respond to such prompts, the autonomous vehicle can predict that the user is comfortable with navigation parameters currently implemented by the autonomous vehicle and continue to implement these navigation parameters accordingly. The autonomous vehicle can similarly continue to implement these navigation characteristics responsive to positive confirmation from the user that the user is comfortable or otherwise not negatively disposed to current autonomous navigation of the autonomous vehicle.

However, if the user does respond directly—and negatively—to this prompt, the autonomous vehicle can automatically modify motion planning and/or navigation parameters implemented by the autonomous vehicle during the remainder of the trip accordingly, as described below.

As described above, the autonomous vehicle can store the user's responses in memory, such as by linking the user's responses to corresponding segments of the current route.

7.3 Post-Ride User Feedback

The autonomous vehicle can additionally or alternatively present a survey related to the user's sentiment to the user—through the display inside the passenger compartment—upon conclusion of the trip. Alternatively, the remote computer system can interface with the native application executing on the user's mobile computing device to present this survey to the user and to record the user's responses.

For example, the autonomous vehicle (or the native application) can present to the user a short list of questions, such as relating to ride comfort, perception of safety, and experienced nausea, etc. The autonomous vehicle can then confirm a peak permitted acceleration and an object offset distance—implemented by the autonomous vehicle during the trip—for the user if the user confirms a high degree of perceived safety. However, if the user indicates a lower perception of safety, the autonomous vehicle can: scan stored navigation data for peak acceleration(s) and minimum external object (e.g., other vehicle, pedestrian) proximity during the user's trip; reduce peak permitted accelerations in the user's profile to below the peak acceleration during the trip; and increase the obstacle avoidance distance in the user's profile to more than the minimum external object proximity during the trip. Similarly, if the user's indicates a feeling of nausea in the post-ride survey, the autonomous vehicle can update the user's profile to include lower peak permitted accelerations and rules for smoother navigation paths.

In another example, the autonomous vehicle (or the native application) can render the trip route on an electronic map and prompt the user to tag or annotate segments of the route with the user's comfort level, nausea, perception of safety, or other relative feedback during these segments of the ride. The user may then tag discrete points or segments along the route that the user recalls as resulting in certain sentiments. The autonomous vehicle can then access trip data corresponding to locations proximal each point or along each segment of this route thus labeled by the user and correlate the user's feedback with these navigation and trajectory data. For example, the autonomous vehicle can retrieve an average speed, peak lateral acceleration, peak longitudinal acceleration, and/or proximity to a nearest detected obstacle within a segment of a route—from the user's last trip—annotated by the user with a negative emotion or feeling. In this example, if the user labels the segment of the route with a feeling of nausea, the autonomous vehicle can: characterize accelerations and a trajectory of the autonomous vehicle over this segment; write a peak permitted acceleration less than peak accelerations along this segment to the user's profile; and write a rule to yield smoother navigation paths than that which occurred over this segment of the route to the user's profile.

Therefore, in this variation, the autonomous vehicle can predict or derive links between sentiment-related feedback provided by the user and certain navigational characteristics or navigational events occurring at the autonomous vehicle, such as according to a rules engine or other model. The autonomous vehicle and/or the remote computer system can then adjust motion planning and/or navigation parameters stored in the user's profile accordingly.

7.4 Hybrid Biosignals and User Feedback

In one variation, the autonomous vehicle collects both biosignal and/or emotion data and feedback from the user ride and refines motion planning parameters for the user based on these data. The autonomous vehicle can then implement these modified motion planning parameters in real-time during this trip; additionally or alternatively, other autonomous vehicles can implement these modified motion planning parameters when occupied by the user during subsequent trips.

In one implementation, during the trip, the autonomous vehicle: records a sequence of video frames via a camera arranged in the autonomous vehicle and facing a passenger compartment in the autonomous vehicle; detects the user in the sequence of video frames; extracts a sequence of features of the user from the sequence of video frames; implements methods and techniques described above to transform the sequence of features into a timeseries of emotions of the user during the trip; and identifies the baseline emotional state of the user—including a positive emotion (e.g., excited, elated, ecstatic, calm, serene, or content)—at the beginning of this timeseries of emotions. In this implementation, the autonomous vehicle can also record a timeseries of navigational characteristics of the autonomous vehicle during the trip, such as: motion of the autonomous vehicle; brake, accelerator, and steering wheel positions of the autonomous vehicle; constellations of object types in the vicinity of the autonomous vehicle; local road and traffic conditions; states of nearby traffic signals; etc. The autonomous vehicle can then implement deep learning, machine learning, regression, clustering, or other data processing techniques to identify correlations between navigational characteristics in the timeseries of navigational characteristics and concurrent emotions of the user in the timeseries of emotions, such as including isolated particular navigational characteristics that occur with high frequency concurrently, just before, or just after degradation of the user's sentiment during the trip. The autonomous vehicle can then implement methods and techniques described above to modify motion planning parameters implemented by the autonomous vehicle, such as in real-time, based on these correlations.

Furthermore, in this implementation, the autonomous vehicle (or the remote computer system) can: generate a map depicting the route traversed by the autonomous vehicle during the trip; link segments of the route depicted in the map to concurrent emotions of the user based on the timeseries of emotions and to concurrent navigational characteristics of the autonomous vehicle based on the timeseries of navigational characteristics during the trip; and then prompt the user to confirm emotions linked to various segments of the route depicted in the map. For example, the autonomous vehicle can: render the map on an interior touchscreen in the autonomous vehicle; overlay the route and the autonomous vehicle's current location on the map; annotate segments of the route with predicted user emotions (e.g., "calm," "nauseated," "anxious") and concurrent navigational characteristics (e.g., "braking," "passing construction zone," "entering school zone," "waiting for pedestrian to cross"); and prompt the user to confirm these predicted emotions and/or confirm a relationship between these emotions and concurrent navigational characteristics by selecting, modifying, or discarding these annotations in (near) real-time. Alternatively, the autonomous vehicle (or the remote computer system) can serve this map, route overlay, and emotional and navigational characteristic annotations to the user's smartphone or other computing device; and the user confirm, modify, or discard these annotations through her smartphone, such as in (near) real-time or upon conclusion of the trip.

The autonomous vehicle (or the remote computer system) can then implement methods and techniques described above and below to: derive correlations between confirmed negative user emotions—linked to certain segments of the route—and a subset of navigational characteristics occurring along these same route segments; and then modify a set of global motion planning parameters for a fleet of autonomous vehicles to deviate from this subset of navigational characteristics correlated with these negative emotions. The autonomous vehicle—and other autonomous vehicles in the fleet—can then implement these modified global motion planning parameters when occupied by the same user and/or other users during subsequent trips.

8. Rider Profile

As described above, the autonomous vehicle can store motion planning parameters—modified based on changes in user sentiment or confirmed based on user sentiment during the trip—in a rider profile associated with the user in Block S160.

During the trip, the autonomous vehicle can also verify that a modification to motion planning parameters executed by the autonomous vehicle improved the user's sentiment (or reduced rate of degradation of the user's sentiment) before writing this modification to the user's profile. For example, after detecting degradation of the user's sentiment, correlation of this degradation of user sentiment with a navigational characteristic, and modifying a motion planning parameter in order to deviate from this navigational characteristic while traversing a first segment of the trip, the autonomous vehicle can autonomously navigate along a second segment of the trip according to this modified motion planning parameter. During this second segment of the trip, the autonomous vehicle can implement methods and techniques described above to derive, access, and/or track the emotional state of the user. If the autonomous vehicle detects an improvement of sentiment of the user during this second segment of the trip, the autonomous vehicle can correlate this improvement of user sentiment with deviation from the foregoing navigational characteristic and thus verify that the modified path planning parameter—which yielded this deviation from the navigational characteristic—improved user sentiment. Accordingly, the autonomous vehicle can write the modified motion planning parameter to the user's profile and upload the user's profile to a remote database.

The autonomous vehicle can also correlate degradation of the user's sentiment with multiple possible navigational characteristics, selectively adjust corresponding motion planning parameters throughout the trip, and verify and discard certain motion planning parameter modifications based on subsequent changes in the user's sentiment. For example, the autonomous vehicle can implement a first motion planning parameter and a second motion planning parameter during a first segment of the trip. Responsive to detecting degradation of user sentiment along this first segment of the trip in Block S140, the autonomous vehicle can correlate this degradation of user sentiment with the first motion planning parameter in Block S142 and modify the first motion planning parameter accordingly in Block S150. Then, during a second segment of the trip, the autonomous vehicle can: implement the modified first motion planning parameter and the original second motion planning parameter to autonomously navigate toward the specified destination location in Block S120; continue to track the user's sentiment (e.g., based on additional biosignals of the user collected by the interior camera or the wearable device worn by the user) in Block S132; detecting a second degradation of user sentiment based on a difference of a second emotional state of the user and a previous emotional state of the user (e.g., the baseline emotional state or an emotional state prior to implementing the modified first motion planning parameter) in Block S140; and then correlate this second degradation of user sentiment with a second navigational characteristic exhibited of the autonomous vehicle during both the first segment and the second segment of the trip in Block S142. Given that further degradation of user sentiment occurred after modifying the first motion planning parameter and that the autonomous vehicle exhibited the second navigational characteristic during this period of user sentiment degradation, the autonomous vehicle can: return the modified first motion planning parameter back to its original value or definition; and modifying a second motion planning parameter predicted to deviate from the second navigational characteristic in Block S150. During a subsequent segment of the trip, the autonomous vehicle can: autonomously navigate toward the destination location according to the original first motion planning parameter and the modified second motion planning parameter in Block S122; and repeat this process to confirm or modify the same or other motion planning parameters implemented by the autonomous vehicle. The autonomous vehicle can also calculate greater confidence scores for modified motion planning parameters and improved user sentiment if these modified motion planning parameters result in improvement of degradation of user sentiment. Finally, the autonomous vehicle can store a final set of motion planning parameters implemented by the autonomous vehicle upon conclusion of the ride and/or store higher-confidence motion planning parameters in the user's profile.

Later, when the user enters a second autonomous vehicle at the beginning of a second trip, the second autonomous vehicle can: access the user's profile; and autonomously navigate toward a second destination location of the second trip according to the modified motion planning parameter stored in the user's profile.

9. Example

In one example, as the autonomous vehicle approaches an obstacle in or near the autonomous vehicle's path (e.g., construction zone), the autonomous vehicle can: detect an increase in the user's heart rate, which may indicate user discomfort; detect the user gripping a grab handle inside the autonomous vehicle, which may indicate fear or anxiety; or detect a change in the user's physiognomy that indicates a heightened sense of fear or anxiety. If the autonomous vehicle has not yet reached the obstacle, the autonomous vehicle can: decrease its speed; set an increased obstacle avoidance distance; recalculate its path according to this increased obstacle avoidance distance; and execute this revised path. As the autonomous vehicle thus modifies its autonomous navigation in (near-) real-time responsive to the user's sentiment change, the autonomous vehicle can also continue to track the user's sentiment to confirm that indicators of fear or anxiety have diminished; if so, the autonomous vehicle can write this new obstacle avoidance distance to the user's profile. However, if the user's increased fear or anxiety persists well past the obstacle, the autonomous vehicle can present a survey to the user to gain further insight into the user's current sentiment, such as by directly querying the user for her perception of safety and providing options for manually modifying navigation parameters of the autonomous vehicle. If the user confirms a sufficient perception of safety, the autonomous vehicle can associate the increased fear or anxiety to external factors and return to the previous obstacle avoidance distance.

In the foregoing example, if the autonomous vehicle has already passed the obstacle upon calculating the revised obstacle avoidance distance, the autonomous vehicle can implement this revised obstacle avoidance distance during the remainder of the trip and implement similar methods to confirm that this revised obstacle avoidance distance has resulted in improved user sentiment when navigating past other obstacles.

Furthermore, if the autonomous vehicle confirms that this revised obstacle avoidance distance results in improved user sentiment throughout the remainder of the trip, the autonomous vehicle can write this revised obstacle avoidance distance to the user's profile; and the same or other autonomous vehicles can implement this increased obstacle avoidance distance when calculating trajectories and navigating past obstacles during future trips with the user.

Alternatively, if the autonomous vehicle detects no or only minimal increase in the user's heart rate, no use of the grab handle, and/or no minimal change in the user's physiognomy as the autonomous vehicle approaches this obstacle, the autonomous vehicle can: interpret this consistent user sentiment as user comfort with the autonomous vehicle's trajectory toward and past the obstacle; and thus confirm the current obstacle avoidance distance in the user's profile Furthermore, in this example, the autonomous vehicle can monitor the user's awareness of the obstacle by tracking the user's eye as the autonomous vehicle approaches the obstacle. If the user's eye position or movement is directed out of the autonomous vehicle and in the direction of an upcoming or nearby obstacle for at least a minimal duration of time (e.g., two seconds), the autonomous vehicle can determine that the user is aware of (i.e., has observed) the obstacle. If the autonomous vehicle also determines that the user has exhibited minimal or no increase in heart rate, perspiration, or other indicator of increased anxiety as the autonomous vehicle approaches and then passes the obstacle, the autonomous vehicle can: confirm that the user is generally comfortable with the autonomous vehicle's avoidance of the obstacle; and can preserve a current obstacle avoidance distance in the user's profile accordingly.

However, if the autonomous vehicle determines that the user is not aware of or otherwise has failed to observe the obstacle, the autonomous vehicle can withhold confirming the user's comfort with the obstacle avoidance distance implemented by the autonomous vehicle. Alternatively, the autonomous vehicle can: correlate the user's lack of awareness with the obstacle with a high degree of user comfort with the autonomous vehicle's autonomous navigation; and then update the user's profile to reflect a smaller obstacle avoidance distance—greater than or equal to a minimal obstacle avoidance distance hardcoded into operation of the autonomous vehicle—accordingly.

Furthermore, if the autonomous vehicle confirms that the user is aware of the obstacle but is also exhibiting indicators of increased fear or anxiety as the autonomous vehicle approaches the obstacle, the autonomous vehicle can: interpret the user's negative shift in sentiment with discomfort with the autonomous vehicle's trajectory toward the obstacle; and increase the obstacle avoidance distance in the user's profile accordingly, as described above.

The autonomous vehicle can implement similar methods and techniques to respond to detected indicators of nausea in the user by: reducing peak forward and lateral accelerations of the autonomous vehicle; smoothing its path; and confirming that these changes in motion planning and navigation parameters have correlated with decreased severity of indicators of nausea in the user (or at least correlated with abatement of further increases in the user's nausea). The autonomous vehicle can also respond to detected indicators of boredom or frustration in the user by: increasing peak forward and lateral accelerations of the autonomous vehicle; reducing weight of a smoothing function applied to the autonomous vehicle's path; increasing peak permitted top speed (such as relative to posted speed limits); and confirming that these changes in motion planning and navigation parameters have correlated with decreased boredom or frustration.

The autonomous vehicle can also execute each of these processes to address fear, anxiety, nausea, frustration, and other user sentiments throughout the trip in order to converge on motion planning and navigation parameters best suited to the user such as for the current trip or more generally, thereby customizing operation of the autonomous vehicle or autonomous vehicles generally for the user.

Furthermore, the remote computer system can: compile motion planning and navigation parameters customized for a corpus of users by a fleet of autonomous vehicles over time; extract trends from these data; and develop a default profile for new users based on these trends. The remote computer system can additionally or alternatively: generate revised global motion planning and navigation parameters for all autonomous vehicles in the fleet or all autonomous vehicles in a geographic region based on these trends; and push these revised global motion planning and navigation parameters to these autonomous vehicles in order to yield improved comfort for users during trips in these autonomous vehicles.

10. Variation: Population Modeling

Figure 3:
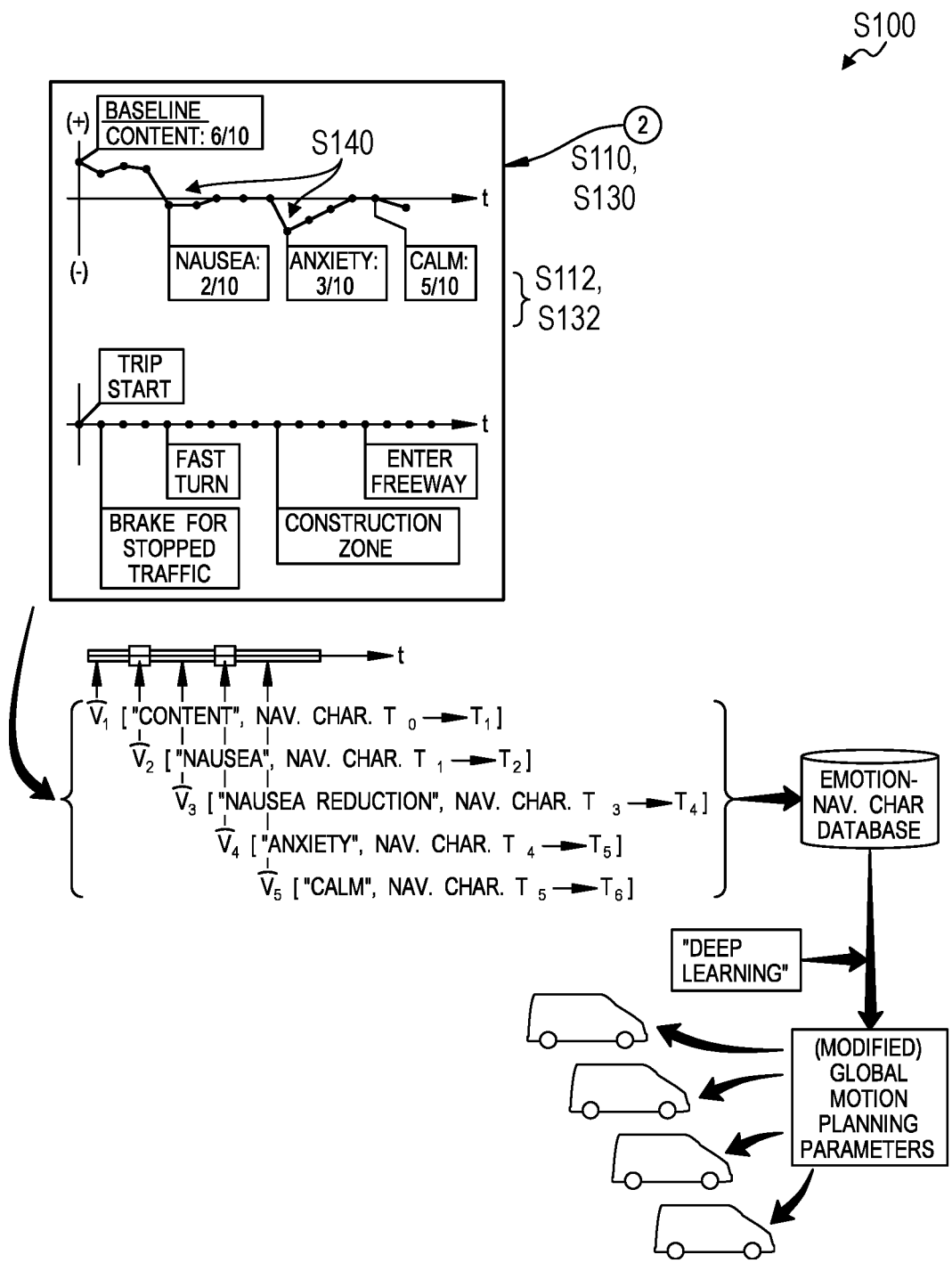
FIG. 3 is a flowchart representation of one variation of the method.

In one variation shown in FIG. 3, the autonomous vehicle collects sentiment and navigational characteristic data during a trip and uploads these data to a remote computer system, such as in real-time or upon conclusion of the trip and in the form of synchronized sentiment and navigational characteristic timeseries. The remote computer system can then: aggregate these sentiment and navigational characteristic data from this trip with sentiment and navigational characteristic data from other trips completed across a fleet of autonomous vehicles; implement deep learning, machine learning, regression, clustering, and/or other data processing techniques to derive correlations between rider sentiments and navigational characteristics of autonomous vehicle trips across a population of riders; and update or modify global motion planning parameters in order to reduce frequency of navigational characteristics correlated with negative rider sentiments and degradation of rider sentiment. The remote computer system can push these updated or modified motion planning parameters to autonomous vehicles in this fleet, which can then implement these updated or modified motion planning parameters during subsequent trips in order to maintain greater levels of rider comfort.

In one implementation, throughout a trip, the autonomous vehicle can track emotions, emotion changes, and/or emotion intensities during the trip. For example, the autonomous vehicle can: record a sequence of video frames via a camera arranged in the autonomous vehicle and facing a passenger compartment in the autonomous vehicle during the trip; detect the user in the sequence of video frames; extract a sequence of features (e.g., facial expressions, eye movements, heart rate, skin temperature) of the user from this sequence of video frames; and then transform this sequence of features into a timeseries of emotions of the user (e.g., calm, nausea, anxiety) during the trip.

The autonomous vehicle can additionally or alternatively access biosignal and/or emotion data from a wearable device worn by the user and store these data as a timeseries of emotions of the user, as described above. The autonomous vehicle can also collect rider feedback from the user, such as via a survey served to the user during the ride (e.g., via the user's smartphone or an interior display in the autonomous vehicle) and/or after the ride (e.g., via the user's smartphone). The autonomous vehicle can then verify or modify the timeseries of user emotions according to these data received from the wearable device and/or based on feedback provided directly by the user.

In this implementation, throughout the trip, the autonomous vehicle can also track navigational characteristics of the autonomous vehicle, such as: motion characteristics of the autonomous vehicle (e.g., acceleration, velocity, geospatial location, angular velocity); autonomous vehicle navigational actions (e.g., turning, braking, accelerating, merging); cabin characteristics (e.g., air temperature, humidity, HVAC setting, window positions, cabin noise, stereo setting); local road characteristics perceived by the autonomous vehicle (e.g., proximity of a construction zone)); local road characteristics stored in a localization map implemented by the autonomous vehicle (e.g., a lane occupied by the autonomous vehicle, approaching a blind turn, approaching an unprotected left turn, proximity of a crosswalk, proximity of a retail shop or other institution); local obstacles perceived by the autonomous vehicle (e.g., a constellation of other vehicles and pedestrians around the autonomous vehicle and their velocities or predicted trajectories); and/or rider demographics (e.g., age, gender, number of riders); etc. The autonomous vehicle can store these navigational characteristics in a "trip feature timeseries" of navigational characteristics or as timestamped navigational features, such as in a buffer or trip file for the trip. The autonomous vehicle can then upload these rider emotion and navigational characteristic data to the remote computer system, such as in real-time or upon conclusion of the trip via a cellular or local wireless network.

The remote computer system can then populate a set of vectors with navigational characteristic data from this trip and label these vectors with corresponding user emotion data. For example, the remote computer system can: segment a trip into a sequence of trip periods, such as spanning 100-meter segments of the route traversed by the autonomous vehicle or spanning ten-second intervals throughout the trip; compile navigational characteristics data spanning each of these trip periods into one trip vector; and label each trip period with a predominate emotion or a constellation of emotions and emotion intensities exhibited by the user during the trip period.

Alternatively, the remote computer system can: identify a set of "emotion periods" in the timeseries of user emotions, wherein each emotion period is characterized by one predominant emotion or emotion intensity range (e.g., greater than or less than 5/10 intensity of anxiety, fear, or serenity) exhibited continuously by the user; and segment the trip feature timeseries into a set of trip feature periods concurrent with this set of emotion periods. For each trip period, the remote computer system can then: compile navigational characteristic data in the trip period into one trip vector; and label the vector with a predominant emotion or emotion intensities exhibited by the user during the concurrent emotion period. In particular, the remote computer system can generate a set of trip vectors, wherein each trip vector represents navigational characteristics during a segment of the trip in which the user exhibits relatively consistent emotions or sentiment and wherein consecutive trip vectors are segmented by changes in user emotions or sentiments, as shown in FIG. 3. For example, the remote computer system can: generate a first trip vector spanning a thirty-second interval leading up to an emotion change (e.g., from calm to anxious; from less than 2/10 fearful to more than 6/10 fearful); and a second trip vector spanning a ten-second interval immediately following the emotion change and in which the user exhibits this different emotion (e.g., anxious; more than 4/10 fearful). The remote computer system can also normalize emotion or sentiment labels for each of these trip vectors (or normalize the timeseries of user emotions) based on the baseline sentiment of the user upon entering the autonomous vehicle at the beginning of the trip.

The remote computer system can repeat this process to generate a corpus of trip vectors for this particular trip and then store this set of trip vectors in a corpus of trip vectors representative of segments of trips completed by autonomous vehicles over time (e.g., thousands of rides in which thousands of different riders occupy hundreds of autonomous vehicles within an autonomous vehicle fleet over days, weeks, or years).

Based on this corpus of trip vectors labeled with (normalized) emotions or sentiments exhibited by users during trip segments represented by these trip vectors, the remote computer system can derive correlations between rider emotions and navigational characteristics. For example, the autonomous vehicle can implement deep learning, machine learning, regression, clustering, and/or other data processing techniques to detect patterns, links, or correlations between vector features (e.g., nearby objects, motion of the autonomous vehicle, upcoming or current navigational actions executed by the autonomous vehicle) and rider emotions, emotion intensities, and/or emotion changes, such as for all riders or for certain rider demographics (e.g., certain age groups and genders).

The remote computer system can then modify motion planning parameters—such as for all autonomous vehicles in the fleet, autonomous vehicles in a certain geographic region, or for certain rider demographics—based on these correlations between rider emotions and navigational characteristics in order to increase frequency and duration of positive emotions and decrease frequency and duration of negative emotions for riders occupying these autonomous vehicles. For example, the autonomous vehicle can: modify global motion planning parameters for autonomous vehicles in the fleet in order to: reduce weights of motion planning parameters associated with or predicted to yield navigational characteristics correlated with negative emotions (e.g., increase offset distances from nearby objects, increase braking distance when approaching stopped traffic); and increase weights of motion planning parameters associated with or predicted to yield navigational characteristics correlated with positive emotions (e.g., increase weight of a smoothing function for executing right turns). The remote computer system can then serve these updated global motion planning parameters to autonomous vehicles in the fleet, which can then implement these global motion planning parameters during subsequent trips, as shown in FIG. 3.

The remote computer system can also derive these correlations between rider emotions and navigational characteristics and confirm or further modify global motion planning parameters accordingly over time. For example, the remote computer system can isolate a correlation between merging in a high-traffic condition and rapid increase in rider anxiety. The remote computer system can then: test this correlation by deploying autonomous vehicles to merge faster and merge slower in similar conditions during subsequent trips; and process rider emotion and navigational characteristic data from these trips to further verify a strength of this correlation between merging speed in high-traffic conditions and increase in rider anxiety.

In another example, the remote computer system can isolate a correlation between braking upon approach to stopped or slowed traffic and rapid increase in rider anxiety or fear. The remote computer system can then: test this correlation by deploying autonomous vehicles to brake sooner and at a reduced rate and vice versa in similar conditions during subsequent trips; and process rider emotion and navigational characteristic data from these trips to further verify a strength of this correlation between braking ahead of stopped or slowed traffic and rider anxiety or fear.

In yet another example, the remote computer system can isolate a correlation between entering a school zone with children present and a slow increase in rider anxiety. The remote computer system can then: test this correlation by deploying autonomous vehicles to navigate through school zones at reduced speeds when children are present; and process rider emotion and navigational characteristic data from these trips to further verify a strength of this correlation between speed through a school zone and rider anxiety.

In another example, the remote computer system can isolate a correlation between a particular location and increase in rider excitement. The remote computer system can then: test this correlation by routing autonomous vehicles closer to this particular location and vice versa; and process rider emotion and navigational characteristic data from these trips to further verify a strength of this correlation between the particular location and rider excitement. Responsive to verifying a strong correlation between this particular location and increased rider excitement, the remote computer system can: identify a retail shop (e.g., a coffee shop) near this particular location; and prompt autonomous vehicles traversing routes near this particular location during future trips to query riders to stop at the retail shop.

The remote computer system can similarly: test correlations between passing road construction and increased rider anxiety by dispatching autonomous vehicles to pass road construction zones at different speeds and offset distances; test correlations between pedestrian proximity and increased rider anxiety by dispatching autonomous vehicles to wait longer for pedestrians and to pass pedestrians at greater offset distances; test correlations between high road speeds and increased rider anxiety by dispatching autonomous vehicles to execute trips at lower maximum speeds and vice versa; etc.

In the foregoing examples, the remote computer system can then further modify motion planning parameters for autonomous vehicles in the fleet based on these additional rider emotional and navigational characteristic data collected by autonomous vehicles during these trips. In particular, the remote computer system can revise motion planning parameters—the entire autonomous vehicle fleet, for autonomous vehicles in certain geographic regions, and/or for certain rider demographics—and push these updated motion planning parameters to these autonomous vehicles over time based on rider emotional and navigational characteristic data collected by these autonomous vehicles.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a human annotator computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method comprising:
   identifying a baseline state of a user of an autonomous vehicle;
   autonomously navigating the autonomous vehicle along a travel path toward a destination location during a trip, the autonomous vehicle moving along the travel path based on at least one motion planning parameter;
   identifying a current state of the user;
   determining a change of sentiment of the user based on a comparison of the baseline state with the current state;
   determining a correlation between the change of sentiment of the user with a movement characteristic of the autonomous vehicle during the trip;
   dynamically customizing operation of the autonomous vehicle by modifying the at least one motion planning parameter based on the correlation between the change of sentiment of the user with the movement characteristic of the autonomous vehicle; and
   updating a rider profile for the user based on the modifying of the at least one motion planning parameter.

2. The method of claim 1, wherein the movement characteristic of the autonomous vehicle corresponds to a proximity of the autonomous vehicle to a fixed obstacle during passing, wherein modifying the at least one motion planning parameter comprises modifying an offset distance.

3. The method of claim 1, wherein the movement characteristic of the autonomous vehicle corresponds to an approach of the autonomous vehicle towards an unmoving object, wherein modifying the at least one motion planning parameter comprises modifying at least one of a stopping distance or a rate of deceleration.

4. The method of claim 1, wherein the movement characteristic corresponds to a turn, wherein modifying the at least one motion planning parameter comprises modifying an angular velocity during a turning operation.

5. The method of claim 1, wherein the change in sentiment of the user includes a degradation of sentiment of the user, wherein the at least one motion planning parameter of the autonomous vehicle is modified to reduce an occurrence of navigational events involving the movement characteristic.

6. The method of claim 1, wherein modifying the at least one motion planning parameter includes modifying a smoothing function to transition between a first navigational action and a second navigational action.

7. The method of claim 1, wherein the baseline state of the user is identified based on at least one of the rider profile associated with the user or a previous state of the user during the trip.

8. The method of claim 1, wherein the current state of the user is determined based biosignals of the user.

9. One or more non-transitory tangible computer-readable storage media storing computer-executable instructions for performing a computer process on a computing system, the computer process comprising:
  identifying a baseline state of a user of an autonomous vehicle, the autonomous vehicle moving along a travel path during a trip based on at least one operational parameter;
  identifying a current state of the user;
  determining a change of sentiment of the user based on a comparison of the baseline state with the current state, the change in sentiment of the user being a degradation of sentiment or an improvement of sentiment;
  determining a correlation between the change of sentiment of the user with an operational characteristic of the autonomous vehicle during the trip; and
  dynamically customizing operation of the autonomous vehicle by modifying the at least one operational parameter based on the correlation between the change of sentiment of the user with the operational characteristic of the autonomous vehicle, wherein the at least one operational parameter is modified to reduce an occurrence of the operational characteristic if the change in sentiment of the user is the degradation of sentiment and the at least one operational parameter is modified to increase the occurrence of the operational characteristic if the change in sentiment of the user is the improvement of sentiment.

10. The one or more non-transitory tangible computer readable media of claim 9, wherein the current state of the user is identified based on a sequence of video frames.

11. The one or more non-transitory tangible computer readable media of claim 9, wherein the current state of the user comprises a timeseries of states of the user during the trip.

12. The one or more non-transitory tangible computer readable media of claim 9, the computer process further comprising:
  identifying a portion of a route for the trip corresponding to the correlation between the change of sentiment of the user with the operational characteristic of the autonomous vehicle; and
  linking a location of the portion of the route to the change in sentiment and the operational characteristic of the autonomous vehicle in a navigation a map.

13. The one or more non-transitory tangible computer readable media of claim 12, the computer process further comprising:
  modifying a set of global motion planning parameters for a fleet of autonomous vehicles based on the navigation map.

14. The one or more non-transitory tangible computer readable media of claim 9, wherein at least one of the baseline state of the user or the current state of the user is identified based on data obtained from a user device associated with the user.

15. The one or more non-transitory tangible computer readable media of claim 9, wherein the current state of the user is identified based on at least one of a facial characteristic, eye movement, or a grabbing motion.

16. A system comprising:
  at least one sensor configured to detect a state of a user of an autonomous vehicle during a trip, the autonomous vehicle moving along a travel path based on at least one motion planning parameter during the trip; and
  at least one processor configured to determine a correlation between a change in sentiment of the user with an operational characteristic of the autonomous vehicle during the trip, the change in sentiment of the user determined based the state of the user, the at least one processor dynamically customizing operation of the autonomous vehicle by modifying the at least one motion planning parameter and customizing a rider profile for the user based on the correlation between the change in sentiment of the user with the operational characteristic of the autonomous vehicle.

17. The system of claim 16, wherein the at least one sensor includes one or more of a camera and a heart rate monitor.

18. The system of claim 16, wherein the at least one motion planning parameter is communicated to the autonomous vehicle.

19. The method of claim 1, wherein the change in sentiment includes at least one of an improvement of sentiment of the user or a degradation of sentiment of the user.

20. The one or more non-transitory tangible computer-readable storage media of claim 14, wherein the user device is a wearable and the data includes at least one of PPG or heart rate, wherein modifying the at least one operational parameter includes generating a motion plan for the autonomous vehicle.

21. The system of claim 16, wherein a motion plan for a subsequent trip is generated based on the rider profile for the user.

22. The method of claim 1, further comprising:
  prompting the user for feedback about the trip;
  obtaining the feedback from the user; and
  updating the rider profile for the user based on the feedback.

* * * * *